(12) United States Patent
Bergman et al.

(10) Patent No.: US 10,136,651 B2
(45) Date of Patent: *Nov. 27, 2018

(54) DE-OILED SABADILLA EXTRACT

(71) Applicant: McLaughlin Gormley King Company, Golden Valley, MN (US)

(72) Inventors: John Thomas Bergman, Saint Louis Park, MN (US); Darrick David Unger, Minnetonka, MN (US)

(73) Assignee: MCLAUGHLIN GORMLEY KING COMPANY, Golden Valley, MN (US)

( * ) Notice: Subject to any disclaimer, the term of this patent is extended or adjusted under 35 U.S.C. 154(b) by 288 days.

This patent is subject to a terminal disclaimer.

(21) Appl. No.: 15/299,852

(22) Filed: Oct. 21, 2016

(65) Prior Publication Data

US 2017/0112142 A1 Apr. 27, 2017

Related U.S. Application Data

(60) Provisional application No. 62/244,913, filed on Oct. 22, 2015.

(51) Int. Cl.
*A61K 36/00* (2006.01)
*A01N 65/40* (2009.01)
*A01N 65/42* (2009.01)

(52) U.S. Cl.
CPC ............ *A01N 65/40* (2013.01); *A01N 65/42* (2013.01)

(58) Field of Classification Search
CPC ....................................................... A61K 36/00
USPC ........................................................... 424/725
See application file for complete search history.

(56) References Cited

U.S. PATENT DOCUMENTS

| | | | |
|---|---|---|---|
| 2,348,949 A * | 5/1944 | Allen | A01N 65/00 424/753 |
| 2,390,911 A | 12/1945 | Allen et al. | |
| 3,078,211 A | 2/1963 | Allison et al. | |
| 6,309,678 B1 | 10/2001 | Kahol et al. | |
| 2015/0216181 A1 | 8/2015 | Hernandez et al. | |

OTHER PUBLICATIONS

International Search Report and Written Opinion issued by the International Bureau in corresponding application No. PCT/US2016/058074 dated Jan. 13, 2017.

* cited by examiner

*Primary Examiner* — Michael V Meller
(74) *Attorney, Agent, or Firm* — Wood, Phillips, Katz, Clark & Mortimer

(57) ABSTRACT

The present invention is directed to methods of producing de-oiled sabadilla extract by removing the oil from sabadilla seeds or a sabadilla extract. The invention also relates to methods for controlling pests by application of de-oiled sabadilla extract to pests' or to their environment.

1 Claim, No Drawings

DE-OILED SABADILLA EXTRACT

FIELD OF THE INVENTION

The present invention is directed to methods of producing de-oiled sabadilla extract and methods of its use as a pesticide.

BACKGROUND OF THE INVENTION

Controlling damaging pests on plants grown to provide human food is a constant struggle for growers. Insects can completely destroy a harvest and can cause catastrophic food shortages or financial ruin for the growers. Although many products are effective against insects that damage plants, the products must also be safe enough to be released into the growing environment and safe enough to be applied to parts of the plants that will eventually be consumed.

Organic farming is increasing in popularity. Organic farming restricts the use of compounds that are used for pest control to encourage sustainability and safety. Insecticides can be used in organic farming if they are considered "natural." Unfortunately, many of the natural insecticides currently available are not potent enough to provide adequate insect control. Further, many of the currently available natural pesticides are not practical to apply or their application is cost prohibitive.

One effective naturally derived insecticide is found in the tissues of many of the plants of the genus *Schoenocaulon*. The species with the longest history of use, and the most readily available, is *Schoenocaulon officinale*. The plant is indigenous to Central and South America and its seeds have been used for centuries for their insecticidal properties. The seeds contain the alkaloids veratridine and cevadine, both of which are known to be active against arthropods.

Usually the dried seeds are ground to a powder and the powder is applied dry or wetted to the insects. The dust from the seeds, however, can cause eye and nasal irritation. Another disadvantage of using the ground seeds is that the alkaloids break down quickly in the sunlight and do not provide any residual protection.

U.S. Pat. Nos. 2,348,949 and 2,390,911 disclose the use of ground sabadilla seeds with beta-butoxy-beta-prime-thio-cyanodiethyl-ether to control houseflies. Further, these patents teach heating the seeds and using them as a powder, or mixing them with kerosene to form a sprayable formulation. Neither of these disclosed mixtures of ground sabadilla seeds would be appropriate for organic farming.

Accordingly, there is a need for new methods of controlling insects. The methods should be potent, safe for growers to apply, safe to beneficial organisms (target specific), and safe for the environment.

SUMMARY OF THE INVENTION

In one aspect, the present invention is directed to methods for creating a de-oiled sabadilla extract.

In another aspect, the present invention is directed to methods for controlling pests comprising applying a de-oiled sabadilla extract to pests or to their environment.

In a further aspect, the present invention is directed to a pesticidal de-oiled sabadilla extract product produced by a process comprising the steps of milling sabadilla seeds or other plant parts, washing the milled sabadilla seeds or other plant parts with at least one extract solvent selected from the group consisting of C5 to C14 alkanes, chlorinated methane, chlorinated ethane, benzene, and benzene derivatives, under agitation to dissolve the sabadilla oil in the extract solvent, and removing the extract solvent and sabadilla oil from the de-oiled sabadilla seed or other plant parts.

In yet another aspect, the present invention is directed to a pesticidal de-oiled sabadilla extract product produced by the process comprising the steps of milling sabadilla seeds or other plant parts, washing the milled sabadilla seeds or other plant parts with at least one seed or plant part solvent selected from the group consisting of methanol, ethanol, glycol ether, ethyl lactate, propanol, butyl lactate, gamma-butyrolactone, and 1-butanol under agitation to dissolve the sabadilla extract in the seed or plant part solvent, removing the seed or plant part solvent and sabadilla extract from the washed milled seeds or other plant parts, removing the seed or plant part solvent from the sabadilla extract, washing the sabadilla extract with at least one extract solvent selected from the group consisting of C5 to C14 alkanes, chlorinated methane, chlorinated ethane, benzene, and benzene derivatives, under agitation to dissolve the sabadilla oil in the extract solvent, and removing the extract solvent and sabadilla oil from the de-oiled sabadilla seed extract.

In a preferred embodiment, the sabadilla extract product is prepared from sabadilla seeds.

DETAILED DESCRIPTION OF THE INVENTION

Applicant has unexpectedly developed new methods for removing oil from sabadilla seeds or other plant parts that produce an extract of the sabadilla seeds that is substantially free from oil. The de-oiled extract is more potent than the ground whole seeds because the oil is now gone which concentrates the alkaloids.

Applicant's methods for production of the de-oiled sabadilla extract are also high yielding and can be easily scaled up for commercial use. The de-oiled sabadilla extract can also be formulated to produce products that are easy to handle and use.

In one embodiment, the present invention is directed to methods for producing de-oiled pesticidal sabadilla extract comprising milling sabadilla seeds or other plant parts, washing the milled sabadilla seeds or other plant parts with at least one extract solvent selected from the group consisting of C5 to C14 alkanes, chlorinated methane, chlorinated ethane, benzene, and benzene derivatives under agitation to dissolve the sabadilla oil in the extract solvent, and removing the extract solvent and sabadilla oil from the de-oiled sabadilla seed or other plant parts.

As used herein, "extract solvent" refers to C5 to C14 alkanes, chlorinated methane, chlorinated ethane, benzene, and/or benzene derivatives. As used herein, "benzene derivatives" refers to a chemical compound derived from benzene wherein one or more hydrogen atoms are replaced with another functional group. Examples of benzene derivatives include phenol, toluene, and aniline.

In a preferred embodiment, the extract solvent is hexane.

Sabadilla seeds and extract may be derived from any species of *Schoenocaulon*. The genus *Schoenocaulon* includes the following species: *Schoenocaulon calcicola, Schoenocaulon caricifolium, Schoenocaulon comatum, Schoenocaulon conzattii, Schoenocaulon dubium* (alt. *Schoenocaulon gracile*), *Schoenocaulon framei, Schoenocaulon ghiesbreghtii* (alt. *Schoenocaulon drummondii, Schoenocaulon yucatanense*), *Schoenocaulon ignigenum, Schoenocaulon intermedium, Schoenocaulon jaliscense, Schoenocaulon macrocarpum* (alt. *Schoenocaulon lauricola*), *Schoenocaulon madidorum, Schoenocaulon megar-*

*rhizum, Schoenocaulon mortonii, Schoenocaulon oaxacense, Schoenocaulon obtusum, Schoenocaulon officinale, Schoenocaulon pellucidum, Schoenocaulon plumosum, Schoenocaulon pringlei, Schoenocaulon rzedowskii, Schoenocaulon tenorioi, Schoenocaulon tenue, Schoenocaulon tenuifolium, Schoenocaulon texanum,* and *Schoenocaulon tigrense.*

In a preferred embodiment, sabadilla seeds can be derived from *S. officinale*).

To optimize solvent penetration and subsequent extraction, the seed coat must be ruptured and the distance between penetrable surfaces of the seed reduced as much as possible. The can be achieved by milling the seeds.

Sabadilla seeds are very difficult to cleanly break into fine pieces. The bulk of the seed is hard and oily and requires a lot of energy to pulverize, producing heat due to high friction. Any suitable milling method can be used. Applicant found that cryogenic hammer milling the seeds was ideal for efficient extraction of the sabadilla oil.

Cryogenic grinding, or cryomilling, most commonly uses dry ice, liquid carbon dioxide or liquid nitrogen to cool the feed material in a mill of an otherwise conventional design (e.g. a cryogenic hammermill.) This super-cooling makes the sabadilla seed more uniformly brittle, in turn making it easier to control particle size. Additionally, the oil in the seed is a solid at the temperature of liquid nitrogen, and does not slow processing speed. This increased friability and solidification of the oil allows for very efficient throughput rates during milling.

Flake milling, most commonly using a roller-type mill, was found to create a milled sabadilla seed that was somewhat more efficient to handle during processing than cryogenically hammer milled seed, but allowed a less efficient extraction. In a flake milling procedure, the seeds are heated to increase plasticity and passed between rollers which flatten the seeds into thin, solvent-penetrable flakes that are still largely one piece. Flaking usually produces a minimal amount of fine particles which hinder efficient processing.

Pin milling may also be used but this technique produces particles which are coarse and require more time to process than other milling products. Conventional, ambient, hammer milling and "Fitz" milling may also be used to produce a sufficiently sized particle, however, throughput rates are generally inefficient and it is difficult to control particle size.

While flake milling's larger particle size overall makes it simplest and easiest to handle during processing, Applicant found that cryogenic hammer milling allowed the creation of sabadilla seed particles over a range of sizes that enable a more efficient extraction of sabadilla oil with only a modest increase in material handling difficulty. Accordingly, Applicant found that cryogenic hammer milling with liquid nitrogen was a superior milling approach for producing sabadilla oil.

The milled sabadilla seeds can be washed with the seed or plant part solvent one time or multiple times. For example, the milled sabadilla seeds can be washed one to ten times. If the seed or plant part solvent is decanted and additional seed or plant part solvent added (additional washes), then the yield is increased.

The milled sabadilla seeds can be washed with at least one extract solvent selected from the group consisting of C5 to C14 alkanes, chlorinated methane, chlorinated ethane, benzene, and benzene derivatives one time or multiple times. For example, the milled sabadilla seeds can be washed one to ten times. If the extract solvent is decanted and additional extract solvent is added (additional washes), then more oil is removed and the purity of the extract is increased.

In an embodiment, the milled sabadilla seeds are washed with at least one extract solvent selected from the group consisting of C5 to C14 alkanes, chlorinated methane, chlorinated ethane, benzene, and benzene derivatives from 1 to 5 times. In a preferred embodiment, the milled sabadilla seeds are washed with the extract solvent from 2 to 5 times. In a most preferred embodiment, the milled sabadilla seeds are washed with the extract solvent 5 times.

During the washes, the milled sabadilla seeds and at least one extract solvent selected from the group consisting of C5 to C14 alkanes, chlorinated methane, chlorinated ethane, benzene, and benzene derivatives should be agitated. This can be done by any method known by those of skill in the art. Applicant found that stirring the milled sabadilla seeds in the extract solvent increased the rate of extraction and was an effective means of agitation.

In another embodiment, the de-oiled sabadilla seed is washed with at least one seed or plant part solvent selected from the group consisting of methanol, ethanol, glycol ether, ethyl lactate, propanol, butyl lactate, gamma-butyrolactone, and 1-butanol to separate the inert seed parts such as the cellulose, hemicellulose, lignin and pectin, from the de-oiled sabadilla extract. After washing, the seed or plant part solvent is separated from the inert seed parts. This can be done, for example, by decanting.

The de-oiled sabadilla seed can be washed with the seed and plant part solvent one time or multiple times. For example, the de-oiled sabadilla seed can be washed one to ten times. If the methanol is decanted and additional methanol is added (additional washes), then the purity of the extract is increased.

In an embodiment, the de-oiled sabadilla seed is washed with the plant and seed part solvent from 1 to 5 times. In a preferred embodiment, the de-oiled sabadilla seed is washed with the seed or plant part solvent from 2 to 5 times. In a most preferred embodiment, the de-oiled sabadilla seed is washed with the seed or plant part solvent 5 times.

During the extraction, the de-oiled sabadilla extract and seed or plant part solvent should be agitated. This can be done by any method known by those of skill in the art. Applicant found that stirring the de-oiled sabadilla seed in the seed or plant part solvent increased the rate of extraction and was an effective means of agitation. The process was most efficient if the stirring was brisk enough to prevent sediment from settling in the extraction vessel (e.g., flask).

As used herein, the "seed or plant part solvent" refers to methanol, ethanol, glycol ether, ethyl lactate, propanol, butyl lactate, gamma-butyrolactone, and/or 1-butanol.

In a preferred embodiment, the seed or plant part solvent is selected from the group consisting of methanol, ethanol, glycol ether, ethyl lactate, and propanol. In a more preferred embodiment, the seed or plant part solvent is methanol.

Methanol can be used at temperatures from about 0 to about 60 degrees Celsius. Applicant found that methanol at lower temperatures required additional extraction time and that temperatures above about 55 to about 60 degrees Celsius resulted in methanol loss and boiling. Applicant found that the optimal temperature for methanol extraction was from about 50 to about 55 degrees Celsius.

In yet another embodiment, the present invention is directed to methods for producing a de-oiled sabadilla extract comprising milling sabadilla seeds or other plant parts, washing the milled sabadilla seeds or other plant parts with at least one seed or plant part solvent selected from the group consisting of methanol, ethanol, glycol ether, ethyl lactate, propanol, butyl lactate, gamma-butyrolactone, and 1-butanol under agitation to dissolve the sabadilla extract in the methanol, removing the methanol and sabadilla extract from the washed milled seeds, removing the seed or plant part solvent from the sabadilla extract, washing the sabadilla extract with at least one extract solvent selected from the group consisting of C5 to C14 alkanes, chlorinated methane, chlorinated ethane, benzene, and benzene derivatives under agitation to dissolve the sabadilla oil in the extract solvent, and removing the extract solvent and sabadilla oil from the de-oiled sabadilla seed or other plant parts.

In a preferred embodiment, the at least one extract solvent selected from the group consisting of C5 to C14 alkanes, chlorinated methane, chlorinated ethane, benzene, and benzene derivatives is hexane.

The sabadilla seed extract can be washed with at least one extract solvent selected from the group consisting of C5 to C14 alkanes, chlorinated methane, chlorinated ethane, benzene, and benzene derivatives one time or multiple times. For example, the sabadilla extract can be washed one to ten times. If the extract solvent is decanted and additional solvent is added (additional washes), then more oil is removed and the purity of the extract is increased.

In an embodiment, the sabadilla seed extract is washed with at least one extract solvent selected from the group consisting of C5 to C14 alkanes, chlorinated methane, chlorinated ethane, benzene, and benzene derivatives from 1 to 5 times. In a preferred embodiment, the sabadilla seed extract is washed with the solvent from 2 to 5 times. In a most preferred embodiment, the sabadilla extract is washed with the solvent 5 times.

During the washes, the sabadilla seed extract and at least one extract solvent selected from the group consisting of C5 to C14 alkanes, chlorinated methane, chlorinated ethane, benzene, and benzene derivatives should be agitated. This can be done by any method known by those of skill in the art. Applicant found that stirring the sabadilla extract in the extract solvent increased the rate of extraction and was an effective means of agitation.

The milled sabadilla seeds can be washed with at least one seed or plant part solvent selected from the group consisting of methanol, ethanol, glycol ether, ethyl lactate, propanol, butyl lactate, gamma-butyrolactone, and 1-butanol one time or multiple times. For example, the milled sabadilla seeds can be washed one to ten times. If the seed or plant part solvent is decanted and additional seed or plant part solvent is added (additional washes), then the purity of the extract is increased.

In an embodiment, the seed or plant part solvent and sabadilla extract are removed from the washed milled seeds by decanting (pouring), pumping, or draining. For example, when the extract is produced on a small scale, the milled seeds settle to the bottom of the flask and the methanol and sabadilla extract can be easily decanted out of the flask. During commercial extraction production, the seed or plant part solvent and sabadilla extract can be removed by methods known by those of skill in the art. For example, the seed or plant part solvent and sabadilla extract could be removed from the washing vessel by draining the seed or plant part solvent and sabadilla extract with the use of a screen, pump, or filter.

In another embodiment, sabadilla oil can be extracted from milled sabadilla seeds using countercurrent extraction. Countercurrent extraction is a commercial scale extraction process typically used in oil seed extraction of seeds such as canola and soy. In brief, countercurrent extraction is a continuous process in which fresh, milled seed is fed through a long solvent bath by conveyor. The seed enters one end and the solvent enters the other, both eventually exiting opposite ends of the apparatus as spent marc (i.e. extracted/depleted seed) and miscella (i.e. solvent with a solute load from the seed).

In an embodiment, the seed or plant part solvent is removed from the sabadilla extract by evaporation, including distillation.

In an embodiment, the at least one extract solvent selected from the group consisting of C5 to C14 alkanes, chlorinated methane, chlorinated ethane, benzene, and benzene derivatives and oil are removed from the de-oiled sabadilla seed extract by decanting (pouring), pumping, or draining. During commercial extraction production, the extract solvent and oil can be removed by methods known by those of skill in the art.

In an embodiment, the milled sabadilla seeds are washed with at least one seed and plant part solvent selected from the group consisting of methanol, ethanol, glycol ether, ethyl lactate, propanol, butyl lactate, gamma-butyrolactone, and 1-butanol from 1 to 5 times. In a preferred embodiment, the milled sabadilla seeds are washed with the seed and plant part solvent from 2 to 5 times. In a most preferred embodiment, the milled Schoenocaulon seeds are washed with seed and plant part solvent 5 times.

During the extraction, the milled sabadilla seeds and seed and plant part solvent should be agitated. This can be done by any method known by those of skill in the art. Applicant found that stirring the milled sabadilla seeds in the seed and plant part solvent increased the rate of extraction and was an effective means of agitation. The process was most efficient if the stirring was brisk enough to prevent the milled sabadilla seeds from settling in the extraction vessel (e.g., flask).

Methanol can be used at temperatures from about 0 to about 60 degrees Celsius. Applicant found that methanol at lower temperatures required additional extraction time and that temperatures above about 55 to about 60 degrees Celsius resulted in methanol loss and boiling. Applicant found that the optimal temperature for methanol extraction was from about 50 to about 55 degrees Celsius.

In a further embodiment, the present invention is directed to a pesticidal de-oiled sabadilla product produced by the process comprising the steps of milling sabadilla seeds or other plant parts, washing the milled sabadilla seeds or other plant parts with at least one extract solvent selected from the group consisting of C5 to C14 alkanes, chlorinated methane, chlorinated ethane, benzene, and benzene derivatives under agitation to dissolve the sabadilla oil in the extract solvent, and removing the extract solvent and sabadilla oil from the de-oiled sabadilla seed and other plant parts.

This product can also include the process step of washing the de-oiled sabadilla extract with at least one seed and plant part solvent selected from the group consisting of methanol, ethanol, glycol ether, ethyl lactate, propanol, butyl lactate, gamma-butyrolactone, and 1-butanol and then removing the seed and plant part solvent.

In an alternative embodiment, the present invention is directed to a pesticidal de-oiled sabadilla product produced by the process comprising the steps of milling sabadilla seeds or other plant parts, washing the milled sabadilla seeds or other plant parts with at least one seed or plant part solvent selected from the group consisting of methanol, ethanol, glycol ether, ethyl lactate, propanol, butyl lactate, gamma-butyrolactone, and 1-butanol under agitation to dissolve the sabadilla extract in the seed or plant part solvent, removing the seed or plant part solvent and sabadilla extract from the washed milled seeds or other plant parts, removing the seed or plant part solvent from the sabadilla extract, washing the sabadilla extract with at least one solvent selected from the group consisting of C5 to C14 alkanes, chlorinated methane, chlorinated ethane, benzene, and benzene derivatives under agitation to dissolve the sabadilla oil in the extract solvent, and removing the extract solvent and sabadilla oil from the de-oiled sabadilla seed or other plant parts.

In a further embodiment, the present invention is directed to methods for controlling pests comprising applying the de-oiled sabadilla extract produced by the methods of the present invention to pests or to the pests' environment.

In another embodiment, the pests controlled are selected from the group consisting of members of the class Insecta (insects), Arachnida subclass Acari (mites), and shell-less terrestrial gastropod mollusks (slugs).

In an embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), fleas (Siphonaptera), caterpillars (Lepidoptera), and early immature stages of beetles (Coleoptera), true bugs (Hemiptera), cockroaches (Blattodea), flies (Diptera) and wasps (Hymenoptera). In a preferred embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), and fleas (Siphonaptera). In a more preferred embodiment, the insects controlled are selected from the group consisting of bed bugs (*Cimex lectularius*), western flower thrips (*Frankliniella occidentalis*), green peach aphids (*Myzus persicae*), and greenhouse whitefly (*Trialeurodes vaporariorum*).

In a preferred embodiment, the mites controlled are two-spotted spider mites (*Tetranychus urticae*).

The de-oiled sabadilla extract is a contact pesticide which means that the extract should be applied directly to the pests or their environment for the most effective control. The extract, or a formulation containing the extract, can be mixed with water and applied with a pressurized system, such as aerosol generators or in a form of ground application, e.g., low pressure boom sprayers, high pressure sprayers, air blast sprayers, low volume air sprayers (mist blowers), hand-operated sprayers and pump sprays. The extract should be applied as a fine spray until the surface is uniformly wet with minimal runoff. In another embodiment, the extract can be formulated, for example, as granules, and applied by broadcast.

As used herein, "de-oiled sabadilla extract" refers to an extract of sabadilla seeds or other plant parts which from which the sabadilla seed oil is removed in order to concentrate the alkaloids.

The de-oiled sabadilla extract of the present invention is distinct from sabadilla seeds in their natural state because the de-oiled sabadilla extract has been isolated from the seed and concentrated. The de-oiled sabadilla extract of the present invention is not present in nature in this form.

As used herein, "controlling pests" refers to decreasing the negative impact of pests on plants or animals to a level that is desirable to the grower or animal.

As used herein, "roller mill" refers to equipment used to decrease the shape of a material by pressing the material with at least one cylindrical roller against another roller or firm surface. A roller mill is one way of producing a flaked seed.

As used herein, "pests' environment" refers to any area that the pest is present during any life stage. One environment likely to be treated by the methods of the present invention includes the plants that the pests are living on and the surrounding soil. The pests' environment may include soil, plants, harvested plants, gardens, fields, greenhouses, or other buildings, and various indoor surfaces and structures, such as furniture including beds, and furnishings including books, clothing, etc.

As used herein, "benzene derivatives" refers to a chemical compound derived from benzene wherein one or more hydrogen atoms are replaced with another functional group. Examples of benzene derivatives include phenol, toluene, and aniline.

As used herein, all numerical values relating to amounts, weight percentages and the like are defined as "about" or "approximately" each particular value, namely, plus or minus 10% ($\pm$10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise. For example, the methods of the present invention are directed to controlling "pests" but this can include control of a single pest (such as a single insect).

The following examples are intended to illustrate the present invention and to teach one of ordinary skill in the art how to use the extracts of the invention. They are not intended to be limiting in any way.

EXAMPLES

Example 1

Sabadilla seeds were flake milled according to the manufacturer's instructions. Two hundred grams of milled seed were added to a three liter flask with two liters of hexane at 40 to 45 degrees Celsius and stirred with a three blade stirrer controlled by an overhead motor. A stirring speed was maintained which prevented any seed fragments from settling in the flask. The system was sealed to limit evaporation loss.

The hexane was decanted off and additional hexane was added to the flask. This step was repeated three additional times for all traces of the oil from the milled seed. A total of six liters of hexane was used. The hexane and remaining sabadilla seed oil (as a solute) were then decanted from the flask.

The hexane removed the oil from the milled seeds and a de-oiled sabadilla extract (which included the milled seeds) remained in the flask.

Example 2

The same procedure as explained in Example 1 was used except that only four total hexane washes were used. Each wash was stirred for one hour each. A de-oiled sabadilla extract was still obtained but the extract was not completely oil-free.

Example 3

The same procedure as explained in Example 1 was used except that only three total hexane washes were used. A de-oiled sabadilla extract was still obtained but the extract was not completely oil-free.

Example 4

The same procedure as explained in Example 1 was used except that only 150 grams of milled seed was used with one hexane wash. A de-oiled sabadilla extract was still obtained but the extract was not completely oil-free.

Example 5

Sabadilla seeds were flake milled according to the manufacturer's instructions. Two hundred grams of milled seed were added to a three liter flask with hexane and stirred with a three blade stirrer controlled by an overhead motor. This step removes the oil from the seeds. A stirring speed was maintained which prevented any seed fragments from settling in the flask. The system was sealed to limit evaporation loss.

The hexane was decanted off and additional hexane was added to the flask. This step was repeated three additional times. The hexane and remaining sabadilla seed oil (as a solute) were then decanted from the flask.

The hexane removed the oil from the milled seeds and a de-oiled sabadilla extract (which included the milled seeds) remained in the flask.

The de-oiled sabadilla extract and milled seeds were then washed with methanol to extract the de-oiled sabadilla seed extract from the solid seed parts. The methanol was decanted off and additional methanol was added to the flask. This step was repeated three additional times.

The decanted methanol and solute were then placed in a new flask. Distillation was used to remove the methanol from the de-oiled sabadilla extract. Standard IKA rotary evaporators were used for the distillation. The flask containing the methanol and solute were loaded into the evaporator and into a heated water bath. The flask was heated to between 50 to 55 degrees Celsius at pressures below atmospheric in order to maximize efficient removal of the methanol without allowing it to boil over into the condenser. The evaporated methanol was thoroughly condensed in an adjoining flask leaving a concentrated, de-oiled sabadilla extract in the flask.

Example 6

Sabadilla seeds were flake milled according to the manufacturer's instructions. Two hundred grams of milled seed were added to a three liter flask with methanol and stirred with a three blade stirrer controlled by an overhead motor. This step separated the solid seed parts, such as cellulose, from the seeds. A stirring speed was maintained which prevented any seed fragments from settling in the flask. The system was sealed to limit evaporation loss.

The methanol was decanted off and additional methanol was added to the flask. This step was repeated three additional times.

The decanted methanol and solute were then placed in a new flask. Distillation was used to remove the methanol. Standard IKA rotary evaporators were used for the distillation. The flask containing the methanol and solute were loaded into the evaporator and into a heated water bath. The flask was heated to between 50 to 55 degrees Celsius in order to maximize efficient removal of the methanol without allowing it to boil over into the condenser. The evaporated methanol was thoroughly condensed in an adjoining flask leaving the concentrated solute/extract.

The concentrated solute/extract was then washed with hexane to remove the oil. The hexane was decanted off and additional hexane was added to the flask. This step was repeated three additional times. What remained in the flask was a concentrated, de-oiled sabadilla extract.

We claim:

1. A method for producing a de-oiled sabadilla extract consisting essentially of: milling sabadilla seeds with cryogenic hammer milling;
    washing the milled sabadilla seeds with at least one extract solvent selected from the group consisting of chlorinated methane, chlorinated ethane, and benzene, under agitation to dissolve the sabadilla oil in the extract solvent; and
    removing the extract solvent and sabadilla oil to yield the de-oiled sabadilla extract.

\* \* \* \* \*